United States Patent [19]

Tuchinskiy et al.

[11] Patent Number: 5,864,743
[45] Date of Patent: *Jan. 26, 1999

[54] MULTI-CHANNEL STRUCTURES AND PROCESSES FOR MAKING STRUCTURES USING CARBON FILLER

[75] Inventors: Lev J. Tuchinskiy; Robert A. Mallia, both of Tucson, Ariz.

[73] Assignee: Materials and Electrochemical Research (MER) Corporation, Tucson, Ariz.

[*] Notice: The term of this patent shall not extend beyond the expiration date of Pat. No. 5,774,779.

[21] Appl. No.: 744,359

[22] Filed: Nov. 6, 1996

[51] Int. Cl.⁶ ........................................... B22F 7/02
[52] U.S. Cl. .................. 419/2; 419/3; 419/4; 419/37; 419/41; 419/45; 419/54; 419/55; 264/56; 264/59; 264/63; 501/81; 501/95; 501/99; 428/550
[58] Field of Search ................... 419/2, 3, 4, 37, 419/41, 45, 54, 55; 264/56, 59, 63; 501/81, 95, 99; 428/550

[56] References Cited

U.S. PATENT DOCUMENTS

| 3,790,654 | 2/1974 | Bagley | 264/177 |
|---|---|---|---|
| 4,772,524 | 9/1988 | Coblenz | 428/699 |
| 4,818,264 | 4/1989 | Langhorst | 65/4.3 |
| 4,965,245 | 10/1990 | Sugimoto | 505/1 |
| 5,181,549 | 1/1993 | Shapovalov | 164/79 |

OTHER PUBLICATIONS

Jones, "Fundamental Principles of Powder Metallurgy," Edward Arnold Publishers Ltd., London, 1960 pp. 340-341.
Zheng et al., "Controlled Porosity Alloys Through Solidification Processing: A Modelling Study," Materials Research Society Symposium Proceedings, vol. 371, Advances in Porous Materials, Pittsburgh, PA. Dec. 1994 pp. 365-370.
Pattnaic et al., "Microstructure of Gasar Porous Ingot," Materials Research Society Symposium Proceedings, vol. 371, Advances in Porous Materials, Pittsburgh, PA, Dec. 1994 pp. 371-376.
Wolla et al, "Mechanical Properties of Gasar Porous Copper," Materials Research Society Symposium Proceedings, vol. 371, Advances in Porous Materials, Pittsburgh, PA, Dec. 1994, pp. 377-382.

*Primary Examiner*—Daniel J. Jenkins
*Attorney, Agent, or Firm*—Jerome M. Teplitz

[57] ABSTRACT

A method for making multi-channel structures suitable for use as filters, catalyst carriers or the like. A composite rod comprising an outer shell and an inner core is formed of respective mixtures of powders. The mixture for the outer shell comprises a sinterable powdered structural material such as ceramics, metals, intermetallics, and a powdered binder. The inner core comprises a powdered carbon channel-forming filler material such as graphite or amorphous carbon, and a powdered binder. The composite rod may be deformed, as by extrusion, to reduce its diameter. A bundle of composite rods is assembled and deformed, as by extrusion, to reduce the diameter of the bundle and of its component composite rods. Further bundles of the reduced diameter bundles of composite rods may be likewise deformed by extrusion to reduce further the diameter of the component composite rods of the successive bundles, thereby also increasing the number of such rods per given cross section area of the bundle. The final assembly of bundles is consolidated and the binder is removed, as by heating, followed by removal of the carbon inner cores of the composite rods of the assembly of bundles by oxidation and sintering of the remaining structure of ceramic or metal, as the case may be.

63 Claims, 2 Drawing Sheets

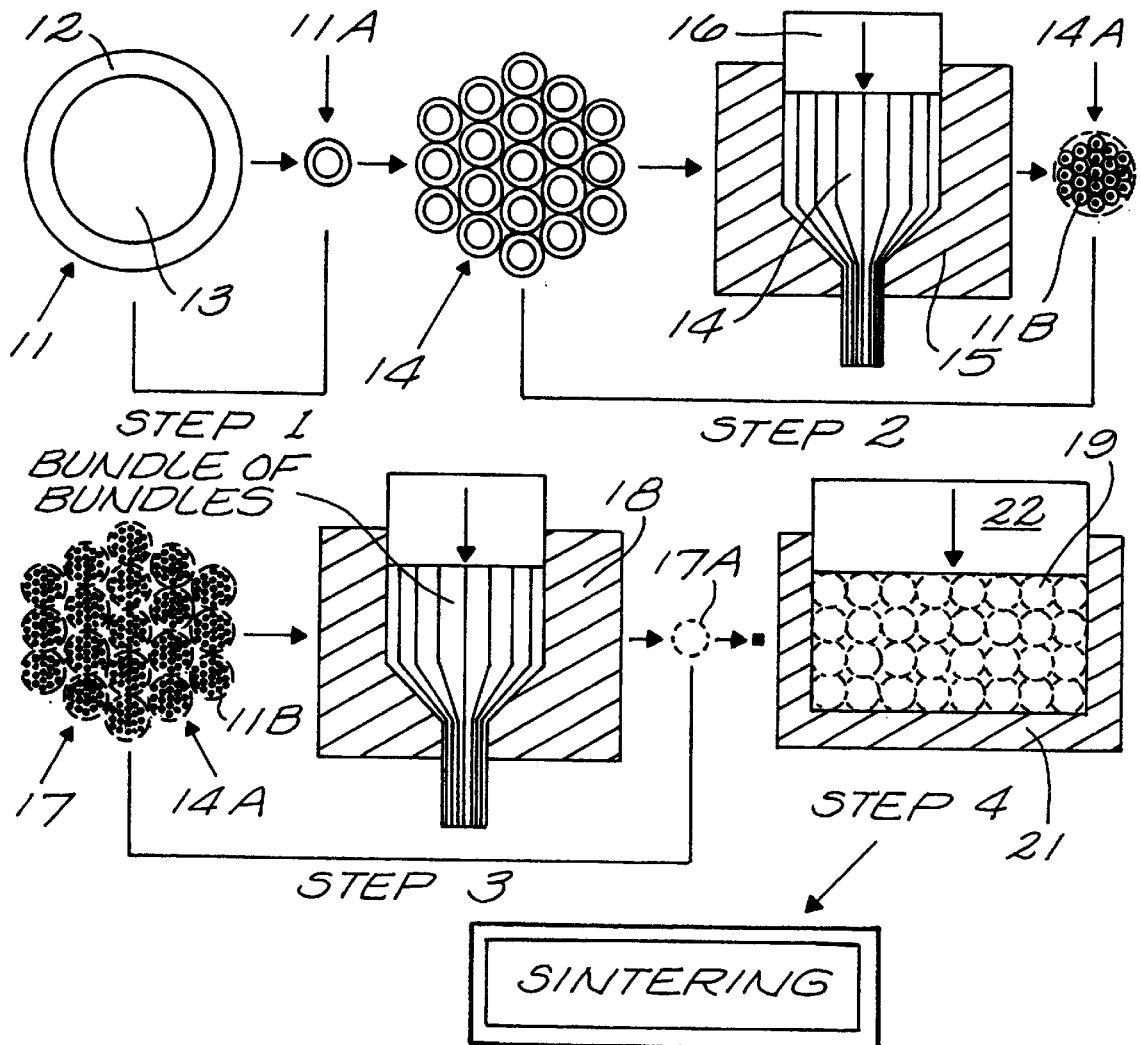
FIG. 1
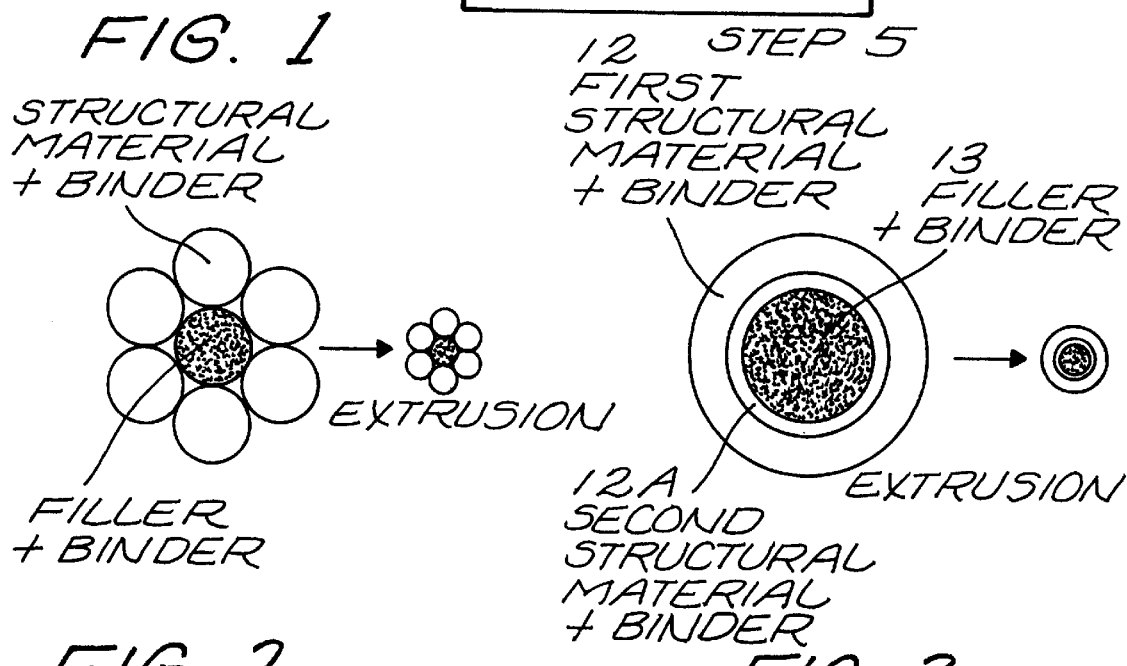
FIG. 2
FIG. 3

STEP 4

STEP 4

MULTI-CHANNEL STRUCTURES AND PROCESSES FOR MAKING STRUCTURES USING CARBON FILLER

The present invention relates to novel methods utilizing carbon filler material for producing multi-channel structures and to structures produced by such methods that are suitable for uses as filters, catalyst carriers, heat exchangers, etc., especially such structures having relatively small channels or apertures ranging from a few microns to a few millimeters in diameter.

BACKGROUND OF THE INVENTION

Various methods are known for making channeled materials. J. Reeman, R. W. Buswell and D. G. Ainley described the method of producing cooling passages in high-temperature turbine blades by the incorporation of cadmium wires in the blade pressing and their subsequent removal by evaporation during sintering, as reported and cited in "Fundamental Principles of Powder Metallurgy" edit by W. D. Jones, and published by Edward Arnold Publisher Limited, London 1960, page 341. This method is very labor and time consuming and does not allow the manufacture of micro-channeled materials with small and uniformly distributed channels.

A directional solidification method called GASAR has been developed for producing solids with controlled porosity [1–3] as disclosed in U.S. Pat. No. 5,181549 issued Jan. 26, 1993. Metals are melted in a given atmosphere of a gas (usually hydrogen), poured into a mold while subjected to a desired pressure, and cooled. As the metal solidifies, the solubility of the dissolved gas goes through a sharp decrease and bubble nucleation occurs. Bubbles which form in the liquid float to a hotter region and are reabsorbed. Bubbles which form at the solid-liquid interface may grow as either isolated or continuous porosity, depending on the solidification conditions. The final microstructure of the porous materials depends on both thermodynamic and kinetic processes. Homogeneous nucleation of bubbles under GASAR processing conditions is impossible, the process is limited to systems which do not form hydrides, the eutectics are highly asymmetric, which leads to an extremely small range of compositions and solidification temperatures where stable eutectic growth is possible. This method does not allow the manufacture of long structures with through microchannels of a given diameter. Moreover, this method cannot be used for producing channels oriented in two or more desired directions.

U.S. Pat. No. 4,818,264 issued Apr. 4, 1989 to Marsha L. Langhorst discloses that hollow glass fibers have been made by drawing down tubes which can be used to produce glass polycapillary materials. Seven glass tubes, 1.8 mm outside diameter by 1.4 mm inside diameter, were placed inside an 8 mm outside diameter by 6 mm inside diameter glass tube and this assembly was drawn with a glass tube drawing machine. The subject patent cites an article by H. D. Pierce Jr. Et al, Technical note "A method for the Preparation of Glass Multicapillary Columns", vol. 17, J. of Chromatographic Science, 5/79, 297, as the source of this work. This method cannot be applied to the powder or brittle materials, such as ceramics, intermetallics, carbon, etc.

Extrusion method for forming thin-walled honeycomb structures was developed by D. Rodney et al. as disclosed in U.S. Pat. No. 3,790,654 issued Feb. 5, 1974. Rodney et al disclose the use of an extrusion die having an outlet face provided with a gridwork of interconnected discharge slots and inlet face provided with a plurality of feed openings extending partially through the die in communication with the discharge slots. Extrudable material is fed to the die under pressure wherein the extrudable materials flow to the interconnected discharge slots communicating with the outlet face, wherein a portion of the material flows laterally within such slots to form a continuous mass before being discharged longitudinally therefrom to form a thin-walled structure having a multiplicity of open passages extending therethrough. The longitudinally discharged mass is rigidified to prevent deformation of the passages. The disadvantage of this method is a very complicated and very expensive tooling, which does not allow the production of the channels less than 0.5–1 mm in diameter and interchannel walls less than 0.2 mm in diameter nor does it allow the production of structures with channels oriented in two or more directions.

Although not concerned with the manufacture of channeled materials, it is noted that some of the procedures used in carrying out the present invention to produce channeled structures, are also used in making monolithic fibrous ceramic structures, as described in U.S. Pat. No. 4,772,524 issued Sep. 20, 1988 to William S. Coblenz.

The Coblenz patent discloses a method of producing fibrous monolithic ceramic product of high density. This product is formed of a plurality of coated fibers and each coated fiber comprises a ceramic core with a ceramic coating. The green body of ceramic materials from which the product is formed is plastically deformed and densified by sintering. However, there is no disclosure or suggestion in this patent for using procedures to produce a multi-channeled structure such as that disclosed and claimed herein.

U.S. Pat. No. 4,965,245, issued Oct. 23, 1990 to Masaru Sugimoto et.a., discloses a method of producing a super-conducting cable or coil comprising a bundle of coated metallic filaments, for example, coated with an oxide, that are drawn and heated in oxidizing atmosphere to form a superconductor. Again, this patent neither discloses nor suggests a process for making channeled structures as disclosed and claimed herein.

SUMMARY OF THE INVENTION

In accordance with the present invention, a multi-channel structure comprising a body of structural material having a plurality of channels therein is produced by forming a composite rod comprising an outer shell formed of a powdered form of the structural material and a binder material and an inner core formed of a powdered form of a channel forming carbon filler material and a binder material, assembling a first bundle of said composite rods in parallel relationship, consolidating said first bundle and reducing the diameter of the individual rods in said first bundle by deforming said first bundle, assembling a plurality of said deformed first bundles with a further bundle of said first bundles and consolidating the further bundle into a final assembly. The binder is then removed from both the outer shell material and the carbon filler core material. The carbon filler core material is removed and the resulting structure is sintered to produce the final structure containing channels as defined by the removed carbon filler material of the cores of the respective composite rods of the final assembly of bundles. The binder and filler core material may be removed before sintering, during the sintering process or after sintering. For example, the binder may be removed by evaporation, decomposition, dissolution, infiltration, melting with following blow out, etc. The filler core material may be removed by oxidation and burning.

In one embodiment, the structural material is a sinterable ceramic powder, such as alumina; the channel forming filler of the core is graphite powder, and the binder of both the core and outer shell is paraffin or wax.

Preferably, the viscosity or yield points of shell and core mixtures at extrusion temperature should be as close as possible to one another.

In the preferred embodiment, the binder is removed by heating. If this is done in an oxidizing atmosphere, the binder should have a melting or boiling point below that of the oxidizing point of the carbon filler core material. The carbon filler core material can also be removed by oxidation through heating at a higher temperature after removal of the binder, and this can be accomplished during the application of the heat used to preform the sintering step, which will require higher temperature than the oxidation point of the carbon filler material.

In another embodiment, the structural material of the shell is formed of a non-carbide forming powdered metal, such as precious metal powders as platinum, palladium, etc. or non-carbide forming metal powders such as magnesium, copper and nickel, and non-carbide forming alloys such as nickel aluminide, and the channel forming filler material of the core is powdered carbon. In this embodiment, the binder has an essentially lower melting point than the oxidation point of the carbon core filler, and may be paraffin or a wax.

In a further embodiment, the composite rod inner core is formed of at least one filler-binder rod formed of the channel forming carbon powder filler material and the binder, and the outer shell is formed by positioning a plurality of rods formed of the mixture of powdered structural and binder materials disposed around and parallel to the inner carbon core material to form a bundle which is deformed, for example, by extrusion to form the composite rod for practicing the method as described above.

In another embodiment, the oxidation of the carbon filler material is controlled by maintaining it in a non-oxidizing atmosphere such as nitrogen or argon while heating the resulting structure to remove the binder, as by melting it, and the temperature of the structure is maintained until the structural components of the structure bond or link to one another to maintain its structural integrity. When the integrity of the structure is assured by such bonding or linking, the non-oxidizing atmosphere is removed and replaced by an oxidizing atmosphere, such as oxygen or air, in order to remove the carbonaceous filler by oxidation, i.e., burning. This may be done apart from or in the course of raising the applied heating temperature to that required for the sintering step.

OBJECTS AND ADVANTAGES OF THE INVENTION

It is an object of the present invention to provide a novel method using powdered materials including carbon powder for producing multi-channel structures comprised of materials such as ceramics, metals, intermetallics and polymers.

It is a further object to provide such method using carbon powder to produce multi-channel structures having relatively small diameter channels suitable for making structures usable as filters, catalyst carriers, heat exchangers, vents, etc.

The methods of the present invention enable the production of novel structures with channels that are of smaller diameter than those of prior methods and also with channels that are formed with relatively thin interchannel walls.

The novel methods of the present invention are simpler and less complex to perform than those of the prior art discussed above which requires the use of relatively expensive equipment including more complex dies, as compared to the simple single orifice dies that can be employed to practice the present invention, to produce structures with a plurality of channels of relatively small diameter.

This method can be used to produce porous polycapillary structures of different ceramics, intermetallics, and metals.

This technique allows control of the final porosity (from a few volume percent to 90 vol. % and more) channel diameter and interchannel wall thickness (from a few microns to a few millimeters) with small tolerance.

This technique can produce not only unidirectional channel structure, but can be adapted to produce bi-directional and three dimensionally porous structures as well.

DESCRIPTION OF THE FIGURES

FIG. 1 is a schematic representation of the steps involved in producing a multi-channel structure according to the present invention.

FIG. 2 is a schematic representation of a procedure comprising a cross sectional view of another embodiment of the composite rod shown in step 1 of FIG. 1.

FIG. 3 is a schematic representation of a cross sectional view of still another embodiment of the composite rod shown in step 1 of FIG. 1, wherein an additional layer comprised of a second structural matrix-binder mixture 12A is interposed between the outer structure matrix-binder layer 12 and the inner core 12.

DESCRIPTION OF THE PREFERRED EMBODIMENTS

Figure 4:
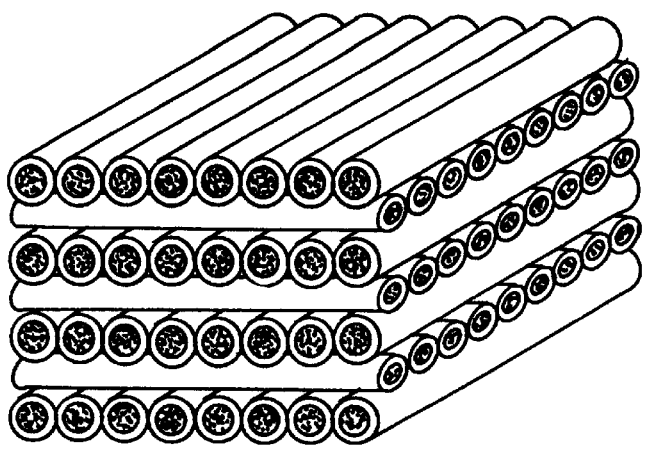
FIG. 4 is a schematic representation showing another embodiment of the final assembly of bundles 19 illustrated in step 4 of FIG. 1 for producing a structure with channels oriented in two perpendicular directions and having different diameters.
Figure 5A:
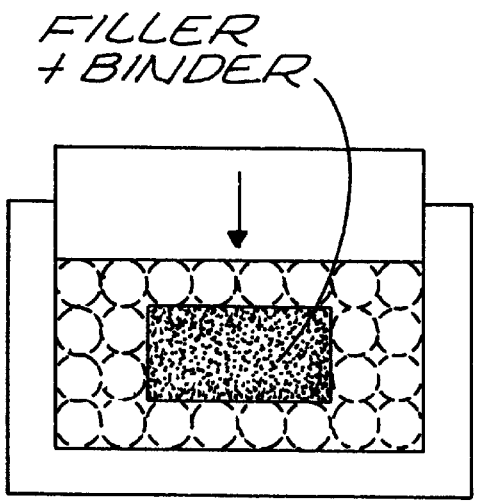
FIGS. 5a and 5b show the other embodiment of step 4 of FIG. 1 arranged to produce a large channel surrounded by multichannel structure (FIG. 5a) and to produce a solid central structure surrounded by multichannel structures (FIG. 5b)
Figure 5B:
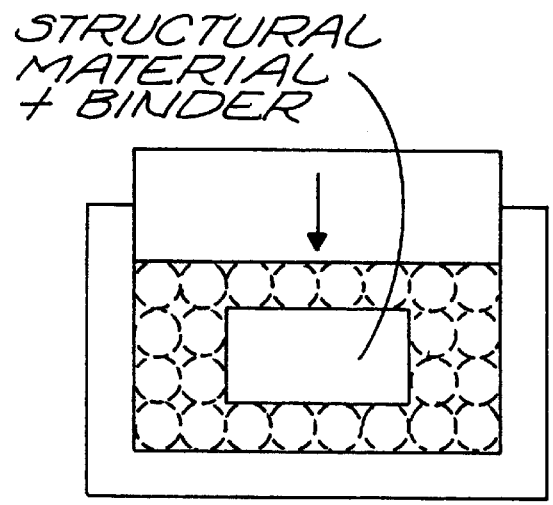

In FIG. 1, there is shown a cross-sectional view of a composite rod 11, comprising an outer shell 12 found of a first mixture comprised of a powdered form of a structural material such as alumina, and a binder material such as paraffin, and an inner core 13 formed of a second mixture comprised of a powdered form of a carbon channel forming filler material such as graphite, and a binder such as paraffin.

The composite rod 11 may be formed, for example, by first producing a tube of the first mixture, for example by extrusion, to form the outer shell 12. The inner core 13 may be separately formed of the second mixture including the powdered carbon, for example by extrusion. The composite rod 11 may then be formed by inserting the inner core 13 into the shell 12.

Alternatively, the mixtures comprising the materials to form the outer shell 12 and the inner core 13 may simultaneously be extruded using a concentric two-channel die to form the composite rod 11.

Once the composite rod 11 is formed, as above, it can be further reduced in diameter, if desired, by extrusion to reduce its diameter to that illustrated as 11–A in FIG. 1.

A bundle 14 of composite rods (11 or 11A) is then assembled as per step 2 illustrated in FIG. 1, wherein the composite rods shown as 11A are disposed parallel to one another, in cross section. A convenient way of producing the several parallel rods (11A) is to produce a long composite rod (11) that may be cut into segments, either before or after reduction in diameter, to 11A, to form the various parallel rods to form the bundle 14.

The bundle 14 of assembled rods is then subjected to deformation, as by extrusion, per step 2 in an extruder 15, shown in cut-away side view, and which has an appropriately sized diameter die to deform and reduce the diameter of the bundle 14, to that shown as bundle 14A as well as the diameter of the individual composite rods 11A comprising the reduced diameter bundle 14A.

As per step 3 illustrated in FIG. 1, a further bundle 17 may be assembled of a plurality of parallel bundles 14A containing the further reduced diameter composite rods 11 B. This further bundle 17 is then subjected to further deformation as per extruder 18, which is provided with a die of appropriate diameter to reduce further the diameter of the further bundle 17 to smaller diameter 17A, as shown per step 3. Of course, the extruder used in steps 1, 2 or 3 may be the same equipment, suitably provided with an extrusion die of the diameter desired for the respective step.

The procedure of assembling bundles of composite rods and deforming those bundles as by extrusion to reduce the diameter of the bundles as well as their constituent composite rods, thereby reducing the diameter of the individual cores 13 and increasing their number per given volume, can be carried out until the desired diameter and number of channel-forming cores is achieved.

The deformation of the assembled bundle of composite rods constitutes a consolidation of the numbers of the bundle, into a rod that may be of circular cross sectional configuration or rectangular or other form. However, it may be desirable to assemble the final bundle into a large assembly not easily consolidated by extrusion. In such case, the final assembly of bundles 17A may, for example, comprise a large bundle assembled in a die 21 for consolidation by compression within the die 21 by a plunger 22, per step 4.

The consolidated bundle 19 is then subjected to heat treatment per step 5, which includes removing the binder i.e. debinding, and removing the carbon filler material by oxidation as well as sintering of the remaining multi-channel green body structure comprised of the channeled structural material.

The selection of the structure materials is determined by the chemical compatibility and oxidation properties of the structure material relative to the carbon filler. In any case, the carbon filler should remain in place until sufficient mechanical integrity develops in the structural material, but it should be removed under conditions that do not deteriorate the properties of the structural materials. Structural materials that require relatively high temperature before it develops sufficient mechanical integrity such as alumina, silicon carbide, and nickel especially benefit from the use of the subject carbon filler material. Carbon filler can be used with the structural materials, which don't form carbides and other chemical compounds in the process of debinding, sintering and filler removing, excluding the cases when their occurrence is envisaged.

The process consists of the following steps (FIG. 1):

Step 1—Production of bi-material rods, 11, consisting, for example, of shell (alumina+binder) and core (carbon filler+binder). The shell comprises a mixture of alumina powder with a binder additive (wax, paraffin, or some thermoplastic polymer like ethylene vinyl acetate, ethylene ethyl acrylate, etc.). The core comprises a mixture of the binder with a carbon powder of channel-forming filler which can be removed afterwards. Powdered graphite or amorphous carbon substances can be used as the fillers. The desirable rods with diameters in the range of 0.1–10 mm will be produced by extrusion of larger diameter (20–200 mm) bi-material rods 11.

Step 2—Assembling the rods into a bundle and re-extruding the bundle: As a result of this step, a green composite blank (rod) that comprises of matrix (alumina+binder) and channel-forming fibers (carbon filler+binder) will be obtained. However, the fibers produced by this stage of extrusion may still have too large a diameter—up to a few hundred microns, hence further reduction in scale may be necessary.

Step 3—Repeating step 2 for further refinement in scale of channels: At the conclusion of this step, the rods obtained will have diameters of 0.1–10 mm, with channel-forming fibers of a diameter of 10–100 microns, depending on the extrusion ratio. This step can be repeated, if necessary, to get even smaller diameter fibers.

Step 4—Assembling the rods produced in step 3 into a bundle and their consolidation in a die, or by cold isostatic pressing, cold extrusion, cold rolling, etc., in order to get the desired green density prior to hot-densification.

Step 5—Densification. This step includes sequentially (1) removing the binder, (2) removing the carbon filler by oxidation, and (3) sintering the multi-channel alumina green body.

The sintering occurs in such a manner that thermally-induced cracks are avoided and provides high density of the interchannel walls in order to get high strength of filter. If paraffin is used as binder, its removal will occur at 150°–350° C. To remove the carbon filler, temperatures of about 300°–500° C. are required to oxidize it. Sintering of alumina will occur at 1500°–1700° C.

By engineering such a multi-channel product through design and control of the microstructure, a variety of ceramic metallic or intermetallic products with properties that are tailored to desired end use can be produced. For example, if product with channel diameter 20 micrometers is required, at stage 1 a bi-material rod with core diameter 0.5 mm and shell diameter 1 mm can be obtained. Then, on the stage 2, a bundle of 1000 of these rods should be collected and extruded from diameter 36 mm to diameter 1 mm, so after stage 2, we will have a diameter of fibers from filler+binder mixture (and hence future channels) in this rod of ~20 micrometers. Step 3 in this case can be excluded. Rods obtained in step 2 should be bundled, pressed (step 4), and sintered (step 5). If smaller diameter channels are required, step 3 may be reincluded.

Thus, the method of this invention is to use repeated coextrusion of a rod structure comprised of a low cost removable inner core comprised of a mixture of carbon filler and binder powders and an outer shell comprised of a mixture of carbon binder powder and of sinterable structural powder material to form a fiber reinforced ceramic matrix green blank to be followed by debinding, removal of the fibers formed by the carbon filler material by oxidation and sintering of the remaining structural matrix. In this way, multichannel structures with controlled diameters and distribution of straight microchannels are formed.

EXAMPLES

Example 1

Producing Multi-Channel Alumina Structure

Alumina powder with an average particle size of 1.3 micron was mixed with a mixture of paraffin plus beeswax binder. The binder contains 90% paraffin and 10% beeswax. The mixture contains 50% binder and 50% alumina powder.

The filler mix was prepared by mixing graphite powder with an average particle size of 20 micron with the same binder as previously described. The loading being 50% binder and 50% graphite.

A tube of the first mixture was extruded to a 60 millimeter outside diameter and 30 millimeter inside diameter.

A rod of the second mixture was extruded that was 30 millimeter in diameter. This was inserted in the tube made from the first mixture.

This composite rod, composed of the alumina-binder tube, which formed the outer shell, and-the graphite-binder rod, which formed the core, was extruded in a die to make a 2 millimeter composite rod.

This 2 millimeter composite rod was cut into segments 100 millimeter long. A bundle of 631 segments were assembled and inserted into a die which had a container and a 90 millimeter diameter cavity and a 30 millimeter outgoing hole and was then extruded. The result is a green body (composite) structure of 30 millimeter outside diameter and with 631 filler graphite and binder fibers having diameter of 0.3 millimeters.

This composite structure was then heated from room temperature to 400° C. at a rate of 0.1° C. per minute for debinding.

Then the composite structure was heated from 400° C. to 1600° C. at a rate of 1.0° C. per minute and held for 2 hours at 1600° C. for the burn out of the graphite filler and the sintering of the alumina structure.

Example 2

Producing Multi-Channel Silicon Carbide

The first mixture was prepared out of 52 vol % sinterable silicon carbide powder with particle size 0.5 micron and 48 vol % binder consisting of 70 wt % polyethylene wax, 25 wt % paraffin wax and 5 wt % beeswax. The second mixture was prepared out of 50 vol % graphite powder (Asbury brand, grade No. Micro 850, particle size −325 mesh) and 50 vol % of the same binder.

The first mixture was extruded through a 20 mm die connected to a 60 mm container to produce 20 mm rods. The second mixture was extruded the same way to produce similar 20 mm rods. On the next step, the rods were assembled into a bundle comprising 7 rods: one—out of second mixture—in the middle, surrounded by six rods made out of first mixture, and inserted into a 60 mm container followed by the extrusion through the attached 20 mm die. On the next step, the composite rod produced during the previous step was cut into 7 pieces of a given length, assembled into a bundle, inserted into a 60 mm container and extruded again through the attached die to produce a further rod with a composite structure: the matrix made out of silicon carbide mixed with binder and seven fibers made out of graphite powder mixed with binder. On the next step, this composite rod was cut into seven pieces as well, bundled, inserted into a die container and extruded through the same die. As a result of this step, a green body structure comprising a silicon carbide/binder matrix and 49 graphite/binder fibers was produced.

The heat treatment consisted of two steps: (1) de-binding (imbedding media—graphite); at 350° C. for 5 hr. at a heating rate of 5°–6° C./hr. followed by gradual heating up to 1100° C. with the heating rate of 10°–12° C./hr. and holding at that temperature for 2 hr., and (2) final sintering (no imbedding media): at 2100° C. for 2 hr. in argon with the heating rate of 10°–12° C./hr. The final step was to heat the sample up to 1400° C. in air to burn out graphite.

As a result, a silicon carbide body structure with 49 through channels was produced.

REFERENCES

1. Y. Zheng, S. Sridar, and K. C. Russel, "Controlled Porosity Alloys Through Solidification Processing: A Modelling Study," *Materials Research Society Symposium Proceedings, Vol.* 371, *Advances in Porous Materials*, Dec. 1994, p. 365–370.
2. A. Pattnaik, S. C. Sanday, C. L. Vold and H. I. Aaronson, "Microstructure of Gasar Porous Ingot," *Materials Research Society Symposium Proceedings, Vol* 371, *Advances in Porous Materials*, Dec. 1994, p. 371–376T.
3. J. M. Wolla and V. Provenzano, "Mechanical Properties of Gasar Porous Copper," Materials Research Society Symposium Proceedings, Vol. 371, *Advances in Porous Materials*, Dec. 1994, p. 377–382.

We claim:

1. A method of producing a solid multi-channeled structure formed of a structural material having a plurality of channels therein comprising the steps of:

a. providing a first mixture comprised of a powdered form of said structural material and a binder material;

b. providing a second mixture comprised of a powdered form of a carbon channel forming filler material and a binder material;

c. forming a composite rod comprising an outer shell formed of said first mixture and an inner core formed of said second mixture by deforming said second mixture to form said core and deforming said first mixture to form said outer shell surrounding said core.

d. assembling a first bundle comprising a plurality of said composite rods in substantially parallel relationship with one another and consolidating said first bundle and reducing the diameter of the individual rods in said first bundle by deforming said bundle;

e. assembling a plurality of said deformed bundles into a further bundle comprising a final assembly in the form of the desired structural configuration;

f. consolidating the further bundle comprising said final assembly while maintaining the filler and binder of the composite rods of said assembly in place;

g. then, removing the binder from both the core material and the shell material of the composite rods comprising the consolidated final assembly;

h. then, sintering the resulting structure comprising the remaining structural material of the outer shells of the composite rods of the final assembly, and, oxidizing the channel-forming carbon filler material to remove it from the inner core of the composite rods comprising the consolidated final assembly; thereby producing a solid structure having a plurality of channels therein as defined by the removed filler material forming the cores of the composite rods comprising the final assembly structure.

2. The method of claim 1, wherein the removal of the carbon channel-forming filler material by oxidation per step (h) is accomplished by heat applied during the sintering step (h).

3. The method of claim 1, wherein the removal of the carbon channel-forming filler material per step (h) is accomplished, by step (i) that is separate from the sintering step (h).

4. The method of claim 1, wherein the diameter of the individual rods of said first bundle of composite rods, after deforming said bundle per step (d), is further reduced prior to being incorporated in said final assembly of step (e) by at least one additional step of deformation in a further bundle comprised of parallel bundles of deformed bundles of reduced diameters.

5. The method of claim 1 wherein the composite rod is formed by deformation of said first and second mixtures per step (c) by extruding said second mixture through an inner orifice and extruding said first mixture through an outer annular orifice to form said outer shell surrounding said core.

6. The method of claim 4 wherein the composite rod is formed by deformation of said first and second mixtures per step (c) by extruding said second mixture through an inner orifice and extruding said first mixture through an outer annular orifice to form said outer shell surrounding said core.

7. The method of claim 1 wherein the step (d) of reducing the diameter of the individual rods in said first bundle by deforming said bundle involves extruding said bundle through an orifice that is smaller than the original circumference of said first bundle.

8. The method of claim 5 wherein the step (d) of reducing the diameter of the individual rods in said first bundle by deforming said bundle through an orifice that is smaller than the original circumference of said first bundle.

9. The method of claim 4 wherein the additional deformation of said bundle of rods to reduce the diameter of the individual rods involves extrusion of said further bundle of rods.

10. The method of claim 8 wherein the additional deformation of said bundle of rods to reduce the diameter of the individual rods involves extrusion of said further bundle of rods.

11. The method of claim 1 wherein the binder material of said first mixture and the binder material of said second mixture are comprised of thermoplastic material.

12. The method of claim 4 wherein the binder material of said first mixture and the binder material of said second mixture are thermoplastic.

13. The method of claim 1 wherein the channel forming material of said second mixture is graphite carbon.

14. The method of claim I wherein the channel forming material of said second mixture is amorphous carbon.

15. The method of claim I wherein the structural material of said first mixture is a sinterable ceramic powder.

16. The method of claim 4 wherein the structural material of said first mixture is a sinterable ceramic powder.

17. The method of claim 11 wherein the structural material of said first mixture is a sinterable ceramic powder.

18. The method of claim 12 wherein the structural material of said first mixture is a sinterable ceramic powder.

19. The method of claim 13 wherein the structural material of said first mixture is a sinterable ceramic powder.

20. The method of claim 14 wherein the structural material of said first mixture is a sinterable ceramic powder.

21. The method of claim 16 wherein the ceramic powder structural material of said first mixture is alumina.

22. The method of claim 17 wherein the ceramic powder structural material of said first mixture is alumina.

23. The method of claim 18 wherein the ceramic powder structural material of said first mixture is alumina.

24. The method of claim 19 wherein the ceramic powder structural material of said first mixture is alumina.

25. The method of claim 20 wherein the ceramic powder structural material of said first mixture is alumina.

26. The method of claim 1, wherein oxidation of the carbon filler material is controlled by maintaining it in a non-oxidizing atmosphere while heating the final assembly to remove the binder followed by replacing the non-oxidizing atmosphere with an oxidizing atmosphere to burn out the carbon filler after the structural integrity of the final assembly is assured by bonding of its components.

27. The method of claim 2 wherein oxidation of the carbon filler material is controlled by maintaining it in a non-oxidizing atmosphere while heating the final assembly to remove the binder followed by replacing the non-oxidizing atmosphere with an oxidizing atmosphere to burn out the carbon filler after the structural integrity of the final assembly is assured by bonding of its components.

28. The method of claim 3 wherein oxidation of the carbon filler material is controlled by maintaining it in a non-oxidizing atmosphere while heating the final assembly to remove the binder followed by replacing the non-oxidizing atmosphere with an oxidizing atmosphere to burn out the carbon filler after the structural integrity of the final assembly is assured by bonding of its components.

29. The method of claim 26, wherein the binder of said first mixture is wax or paraffin.

30. The method of claim 26 wherein the binder of said second mixture is wax or paraffin.

31. The method of claim 29, wherein the binder of said second mixture is also wax or paraffin.

32. The method of claim 1, wherein the step (e) of assembling the extruded bundles into the final assembly involves positioning the respective bundles in layers that are substantially parallel to one another, whereby the resulting solid structure of the sintering step (h) contains a plurality of parallel channels in layers that are in substantially parallel relationship, contains a plurality of parallel channels from one side of the structure to another.

33. The method of claim 4, wherein the step (e) of assembling the extruded bundles into the final assembly involves positioning the respective bundles in parallel relationships, whereby the resulting solid structure of the sintering step (h) contains plurality of parallel channels from one side of the structure to another.

34. The method of claim 5, wherein the step (e) of assembling the extruded bundles into the final assembly involves positioning the respective bundles in layers that are substantially parallel to one another, whereby the resulting solid structure of the sintering step (h) contains a plurality of parallel channels in layers that are substantially parallel from one side of the structure to another.

35. The method of claim (1), wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

36. The method of claim 4, wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

37. The method of claim 5, wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

38. Solid multi-channel structure produced by the method of claim 32.

39. Solid multi-channel structure produced by the method of claim 33.

40. Solid multi-channel structure produced by the method of claim 34.

41. Solid multi-channel structure produced by the method of claim 35.

42. Solid multi-channel structure produced by the method of claim 36.

43. Solid multi-channel structure produced by the method of claim 37.

44. The method of claim 1, wherein the binder material of said first and second mixtures is paraffin and beeswax, the filler material is powdered graphite, wherein the step of removing the binder from the core and shell materials of the consolidated final assembly involves subjecting the consolidated final assembly to heat in the range of 150° C.–350° C., and wherein the step (I) of removing the filler material from the consolidated final assembly involves subjecting the consolidated final assembly to heat in the range of 300° C.–500° C., and wherein the curing step (I) involves sintering by subjecting the remaining structures of the final assembly to heat in the range of 400° C.–1600° C. to oxidize the carbon filler and sinter the alumina structure.

45. The method of claim 1 wherein the structural material of said first mixture consists essentially of powdered metal.

46. The method of claim 4, wherein the structural material of said first mixtures consists essentially of powdered metal.

47. The method of claim 45 wherein the powdered metal of said first mixture consists essentially of powdered copper.

48. The method of claim 46 wherein the powdered metal of said first mixture consists essentially of powdered copper.

49. The method of claim 45, wherein the powdered metal of said first mixture consists essentially of powdered nickel.

50. The method of claim 46 wherein the powdered metal of said first mixture consists essentially of powdered nickel.

51. The method of claim 45 wherein the powdered metal of said first mixture consists essentially of powder selected from among Pt, Pd, Ag, and Au.

52. The method of claim 46, wherein the powdered metal of said first mixture consists essentially of powder selected from among Pt, Pd, Ag and Au.

53. The method of claim 45, wherein the powdered metal of said first mixture consists essentially of powdered magnesium.

54. The method of claim 32, wherein the first mixture containing the powdered form of said structural material comprises a catalyst.

55. The method of claim 35, wherein the first mixture containing the powdered form of said structural material comprises a catalyst.

56. The method of claim 1, wherein the step (c) of forming a composite rod comprising an outer shell formed of said first mixture and an inner core formed of said second mixture involves the preliminary steps of:

(i) forming a plurality of structure-binder rods comprised of said first mixture;

(ii) forming at least one filler-binder rod comprised of said second mixture; and (iii) forming the composite rod of step (c) of claim I by assembling a bundle of parallel rods wherein the core is comprised of at least one of said filler-binder rods and the outer shell is comprised of a plurality of said structure-binder rods disposed around the core and wherein the assembled bundle of the parallel rods is deformed per step (c) to form the composite rod.

57. The method of claim 56, wherein the composite rod of step (c)(iii) is formed by deforming the assembled bundle of parallel rods by extrusion.

58. The method of claim 56, wherein the structural material of said first mixture is a sinterable ceramic powder.

59. The method of claim 58, wherein the sinterable ceramic powder is alumina.

60. The method of claim 58, wherein the sinterable ceramic powder is silicon carbide powder.

61. The method of claim 56 wherein the composite rod formed per step (c) comprises an intermediate layer between the outer shell and the inner core and which is comprised of a third mixture consisting of a powdered form of a second structural material and a binder material and which involves the additional preliminary steps of (iv) forming a plurality of rods of said catalyst-binder material, (v) assembling a plurality of said second structural material-binder rods in said bundle of parallel rods disposed parallel to and between the core and the structure-binder rods comprising the outer shell of the assembled bundle of parallel rods.

62. The method of claim 32 wherein certain of the respective bundles contain parallel channels of different diameter than the diameter of the channels of certain other bundles.

63. The method of claim 35 wherein the channels of the alternately transverse layers are of different diameter.

* * * * *